(12) United States Patent
Brooks et al.

(10) Patent No.: US 7,107,992 B2
(45) Date of Patent: Sep. 19, 2006

(54) SYSTEM AND METHOD FOR PREVENTING CLOSURE OF PASSAGEWAYS

(75) Inventors: Stephen Nelson Brooks, San Mateo, CA (US); Jed E. Black, Stanford, CA (US)

(73) Assignee: Pavad Medical, Inc., Fremont, CA (US)

( * ) Notice: Subject to any disclaimer, the term of this patent is extended or adjusted under 35 U.S.C. 154(b) by 365 days.

(21) Appl. No.: 10/679,935

(22) Filed: Oct. 6, 2003

(65) Prior Publication Data

US 2004/0112390 A1    Jun. 17, 2004

Related U.S. Application Data

(60) Provisional application No. 60/415,995, filed on Oct. 4, 2002.

(51) Int. Cl.
*A61F 5/56* (2006.01)
(52) U.S. Cl. .................. 128/848; 128/859; 128/899; 602/902; 623/11.11; 600/12
(58) Field of Classification Search ............... 128/848, 128/859–863, 899; 600/12, 15; 602/902; 623/9, 11
See application file for complete search history.

(56) References Cited

U.S. PATENT DOCUMENTS

| 4,978,323 | A | 12/1990 | Freedman ............ 600/12 |
| 5,015,538 | A | 5/1991 | Krause et al. |
| 5,117,816 | A | 6/1992 | Shapiro et al. |
| 5,176,618 | A | 1/1993 | Freedman ............ 600/12 |
| 5,199,424 | A | 4/1993 | Sullivan et al. |
| 5,245,995 | A | 9/1993 | Sullivan et al. |
| 5,268,082 | A | 12/1993 | Oguro et al. |
| 5,284,161 | A | 2/1994 | Karell |
| 5,479,944 | A | 1/1996 | Petruson |
| 5,509,888 | A | 4/1996 | Miller |
| 5,522,382 | A | 6/1996 | Sullivan et al. |
| 5,551,418 | A | 9/1996 | Estes et al. |
| 5,823,187 | A | 10/1998 | Estes et al. |
| 5,873,363 | A | 2/1999 | Esmailzadeh |
| RE36,120 | E | 3/1999 | Karell |
| 5,901,704 | A | 5/1999 | Estes et al. |

(Continued)

FOREIGN PATENT DOCUMENTS

DE            4412190 A1      10/1995

(Continued)

OTHER PUBLICATIONS

Nelson et al., "Magnetic Airway Implants for the Treatment of Obstructive Sleep Apnea Syndrome", Dec. 16, 2005, Otolaryngology-Head and Neck Surgery Clinic, pp. 1-2. Printed Jan. 16, 2006.*

(Continued)

*Primary Examiner*—Henry Bennett
*Assistant Examiner*—Amanda Wieker
(74) *Attorney, Agent, or Firm*—Wilson Sonsini Goodrich and Rosati

(57) ABSTRACT

A system for treating sleep-related breathing disorders. In one embodiment, the system includes a first magnetically susceptible material attached to a left lateral pharyngeal wall and a second magnetically susceptible material attached to a right lateral pharyngeal wall. The second magnetically susceptible material is positioned opposite the first magnetically susceptible material across an upper airway. The system further includes a first magnet disposed outside the body and lateral to the first magnetically susceptible material, and a second magnet disposed outside the body and lateral to the second magnetically susceptible material.

7 Claims, 8 Drawing Sheets

U.S. PATENT DOCUMENTS

| | | | |
|---|---|---|---|
| 5,904,141 | A | 5/1999 | Estes et al. |
| 5,970,975 | A | 10/1999 | Estes et al. |
| 5,980,998 | A | 11/1999 | Sharma et al. |
| 5,988,171 | A | 11/1999 | Sohn et al. |
| 6,092,523 | A | 7/2000 | Belfer |
| 6,098,629 | A | 8/2000 | Johnson et al. |
| 6,109,852 | A | 8/2000 | Shahinpoor et al. |
| 6,190,893 | B1 | 2/2001 | Shastri et al. |
| 6,212,435 | B1 | 4/2001 | Lattner et al. |
| 6,250,307 | B1 | 6/2001 | Conrad et al. |
| 6,257,234 | B1 | 7/2001 | Sun |
| 6,376,971 | B1 | 4/2002 | Pelrine et al. |
| 6,379,393 | B1 | 4/2002 | Mavroidis et al. |
| 6,390,096 | B1 | 5/2002 | Conrad et al. |
| 6,401,717 | B1 | 6/2002 | Conrad et al. |
| 6,408,851 | B1 | 6/2002 | Karell |
| 6,415,796 | B1 | 7/2002 | Conrad et al. |
| 6,431,174 | B1 | 8/2002 | Knudson et al. |
| 6,439,238 | B1 | 8/2002 | Brenzel et al. |
| 6,450,169 | B1 | 9/2002 | Conrad et al. |
| 6,453,905 | B1 | 9/2002 | Conrad et al. |
| 6,454,803 | B1 | 9/2002 | Romo, III |
| 6,467,485 | B1 | 10/2002 | Schmidt |
| 6,475,639 | B1 | 11/2002 | Shahinpoor et al. |
| 6,502,574 | B1 | 1/2003 | Stevens et al. |
| 6,513,530 | B1 | 2/2003 | Knudson et al. |
| 6,513,531 | B1 | 2/2003 | Knudson et al. |
| 6,514,237 | B1 | 2/2003 | Maseda |
| 6,516,806 | B1 | 2/2003 | Knudson et al. |
| 6,523,541 | B1 | 2/2003 | Knudson et al. |
| 6,523,542 | B1 | 2/2003 | Knudson et al. |
| 6,523,543 | B1 | 2/2003 | Conrad et al. |
| 6,529,777 | B1 | 3/2003 | Holmstrom et al. |
| 6,545,384 | B1 | 4/2003 | Pelrine et al. |
| 6,546,936 | B1 | 4/2003 | Knudson et al. |
| 6,569,654 | B1 | 5/2003 | Shastri et al. |
| 6,578,580 | B1 | 6/2003 | Conrad et al. |
| 6,583,533 | B1 | 6/2003 | Pelrine et al. |
| 6,586,859 | B1 | 7/2003 | Kornbluh et al. |
| 6,601,584 | B1 | 8/2003 | Knudson et al. |
| 6,601,585 | B1 | 8/2003 | Conrad et al. |
| 6,618,627 | B1 | 9/2003 | Lattner et al. |
| 6,619,290 | B1 | 9/2003 | Zacco |
| 6,626,181 | B1 | 9/2003 | Knudson et al. |
| 6,628,040 | B1 | 9/2003 | Pelrine et al. |
| 6,629,527 | B1 | 10/2003 | Estes et al. |
| 6,634,362 | B1 | 10/2003 | Conrad et al. |
| 6,636,767 | B1 | 10/2003 | Knudson et al. |
| 6,664,718 | B1 | 12/2003 | Pelrine et al. |
| 6,667,825 | B1 | 12/2003 | Lu et al. |
| 6,679,836 | B1 | 1/2004 | Couvillon, Jr. |
| 6,707,236 | B1 | 3/2004 | Pelrine et al. |
| 6,742,524 | B1 | 6/2004 | Knudson et al. |
| 6,748,951 | B1 | 6/2004 | Schmidt |
| 6,749,556 | B1 | 6/2004 | Banik |
| 6,768,246 | B1 | 7/2004 | Pelrine et al. |
| 6,770,027 | B1 | 8/2004 | Banik et al. |
| 6,781,284 | B1 | 8/2004 | Pelrine et al. |
| 6,812,624 | B1 | 11/2004 | Pei et al. |
| 6,835,173 | B1 | 12/2004 | Couvillon, Jr. |
| 6,955,172 | B1 * | 10/2005 | Nelson et al. ............... 128/848 |
| 2002/0173848 | A1 | 11/2002 | Sachs |
| 2003/0015198 | A1 | 1/2003 | Hecke et al. |
| 2003/0140930 | A1 | 7/2003 | Knudson et al. |
| 2003/0149445 | A1 | 8/2003 | Knudson et al. |
| 2003/0149488 | A1 * | 8/2003 | Metzger et al. .......... 623/23.64 |
| 2003/0192556 | A1 | 10/2003 | Conrad et al. |
| 2003/0196669 | A1 | 10/2003 | Conrad et al. |
| 2004/0016433 | A1 | 1/2004 | Estes et al. |
| 2004/0019368 | A1 | 1/2004 | Lattner et al. |
| 2004/0020497 | A1 | 2/2004 | Knudson et al. |
| 2004/0020498 | A1 | 2/2004 | Knudson et al. |
| 2004/0045555 | A1 * | 3/2004 | Nelson et al. ............... 128/848 |
| 2004/0045556 | A1 * | 3/2004 | Nelson et al. ............... 128/848 |
| 2004/0073272 | A1 | 4/2004 | Knudson et al. |
| 2004/0134491 | A1 | 7/2004 | Pflueger et al. |
| 2004/0139975 | A1 * | 7/2004 | Nelson et al. ............... 128/848 |
| 2004/0149290 | A1 * | 8/2004 | Nelson et al. ............... 128/848 |
| 2004/0172054 | A1 | 9/2004 | Metzger et al. |
| 2005/0004417 | A1 * | 1/2005 | Nelson et al. ................ 600/12 |
| 2005/0115572 | A1 * | 6/2005 | Brooks et al. ............... 128/863 |
| 2005/0121039 | A1 * | 6/2005 | Brooks et al. ............... 128/863 |
| 2005/0159637 | A9 * | 7/2005 | Nelson et al. ................ 600/12 |
| 2005/0199248 | A1 * | 9/2005 | Pflueger et al. ............. 128/848 |
| 2005/0268919 | A1 * | 12/2005 | Knudson et al. ............ 128/848 |
| 2005/0284485 | A9 * | 12/2005 | Nelson et al. ............... 128/848 |

FOREIGN PATENT DOCUMENTS

| | | |
|---|---|---|
| EP | 0312368 B1 | 4/1989 |
| EP | 0743076 B1 | 11/1996 |
| EP | 1306104 A2 | 5/2003 |
| WO | WO 88/10108 A1 | 12/1988 |
| WO | WO 96/11653 A1 | 4/1996 |
| WO | WO 97/26039 A1 | 7/1997 |
| WO | WO 01/19301 A1 | 3/2001 |
| WO | WO 02/13738 A1 | 2/2002 |
| WO | WO 02/056876 A2 | 7/2002 |
| WO | WO 02/076341 A2 | 10/2002 |
| WO | WO 02/076352 A1 | 10/2002 |
| WO | WO 02/076353 A1 | 10/2002 |
| WO | WO 02/076354 A1 | 10/2002 |
| WO | WO 03/041612 A2 | 5/2003 |
| WO | WO 03/065947 A1 | 8/2003 |
| WO | WO 2004/043288 A2 | 5/2004 |

OTHER PUBLICATIONS

PCT International Search Report, International Application No. PCT/US 03/31605, dated Mar. 18, 2004.

Carley, David W. et al. 1997. Adenosine A1 Receptor Agonist GR79236 Suppresses Apnea During All Sleep Stages in the Rat. *Sleep.* 20 (12): 1093-8.

Degaspari, John. Hot Stuff: Advanced Materials are Moving Out of the Lab and into the Commercial World. Mechanical Engineering, Feature Article, p. 40; Dec. 2002. http://www.memagazine.org/backissues/dec02/features/hotstuff/hotstuff.html. 9 pages (accessed on Feb. 27, 2006).

Flageole, Helene et al. 1995. Diaphragmatic Pacing in Children with Congenial Central Alveolar Hypoventilation Syndrome. *Surgery.* 118 (1): 25-8.

Grisius, Richard J. 1991. Maxillofacial Prosthetics. *Current Opinion in Dentistry.* 1 (2): 155-9.

Hansen, Helle et al. 1992. Undine's Syndrom (Alveolaer Hypoventilation). *Ugeskr Laeger.* 154 (31): 2160-1 (in Danish w/ English Summary on p. 2161).

Ilbawi, Michel N. et al. 1981. Diaphragm Pacing in Infants and Children: Report of a Simplified Technique and Review of Experience. *The Annals of Thoracic Surgery.* 31 (1): 61-5.

Kane, P.M. et al. 1983. Alloplastic Implants of the Larynx. *Arch Otolaryngol.* 109: 648-52.

Maurer, Joachim T. et al. 2005. Palatal Implants for Primary Snoring: Short-Term Results of a New Minimally Invasive Surgical Technique. *Otolaryngology-Head and Neck Surgery.* 132 (1): 125-31.

Nasaw, Daniel. 2004. As Sufferers of Sleep Apnea Grow, A Less-Invasive Treatment Arises. http://www.mdhealthnotes.net/04-918_sleep_apnea.html (accessed on Feb. 27, 2006).

Nordgard, Stale et al. 2004. Palatal Implants: A New Method for the Treatment of Snoring. *Acta Otolaryngol.* 124 (8): 970-5.

Ogura, Keisuke. Preparation Procedure: Ion-Exchange Polymer Metal Composites (IPMC) Membranes. Osaka National Research Institute, AIST, Japan. http://ndeaa.jpl.nasa.gov/nasa-nde/lommas/eap/IPMC_PrepProcedure.htm (accessed Feb. 24, 2006).

Ouelette, Jennifer. Smart Fluids Move into the Marketplace: Magento- and Electro-Rheological Fluids Find New Uses. *The Industrial Physicist Magazine*, vol. 9, Issue 6, p. 14, Dec. 2003/Jan. 2004. http://www.aip.org/tip/INPHF/vol-9/iss-6/p14.htm. 8 pages (accessed on Feb. 27, 2006).

Pavel, Frank et al. 1994. Contemporary oral and Maxillofacial Surgery. *Journal of the California Dental Association.* 22 (4): 35-8, 40, 42-6.

Preis, Carsten et al. 2001. Removal of the Connector on the Laryngeal Mask Airway Provides a Useful Alternative to the Intubating Laryngeal Mask. *Canadian Journal of Anaesthesia.* 48 (6): 600-3.

Sanna, N. et al. 2004. Prolonged Asystolia in a Young Athlete: A Case of Sinus Arrest During REM Sleep. *International Journal of Sports Medicine.* 25 (6): 457-60.

Troyk, Philip R. 1999. Injectable Electronic Identification, Monitoring, and Stimulation Systems. *Annual Review of Biomedical Engineering.* 1: 177-209.

Villain, E. et al. 2000. Stimulation Cardiaque Dans Les Spasmes Du Sanglost De L'enfant [Cardiac Pacing in Children with Breath-Holding Spells]. *Archives Des Maladies Du Coeur Et Des Vaisseaux.* 93 (5): 547-52. (In French, w/ English Summary).

Hedge, Anant V. et al., U.S. Appl. No. 10/946,435 entitled "Airway Implant and Methods of Making and Using", filed Sep. 21, 2004.

Hedge, Anant V. et al., U.S. Appl. No. 11/233,493 entitled "Airway Implant and Methods of Making and Using", filed Sep. 21, 2005.

Hedge, Anant V. et al., entitled "Airway Implant Sensors and Methods of Making and Using the Same", filed Feb. 15, 2006.

\* cited by examiner

SYSTEM AND METHOD FOR PREVENTING CLOSURE OF PASSAGEWAYS

CROSS-REFERENCE TO RELATED APPLICATIONS

This application claims benefit of U.S. provisional patent application Ser. No. 60/415,995, filed Oct. 4, 2002, which is herein incorporated by reference.

BACKGROUND OF THE INVENTION

1. Field of the Invention

Embodiments of the present invention generally relate to prevention of abnormal breathing sounds (e.g., snoring), adverse consequences, illness or death in persons due to partial or complete blockage of the upper airway.

2. Description of the Related Art

A common and potentially serious disorder in humans involves involuntary closure of the airway during sleep. This disorder is known as "sleep-disordered breathing" or "obstructive sleep apnea" (OSA). In persons with OSA, there is involuntary closure or reduction in caliber of a portion of the airway that connects the atmosphere to the lungs. The upper portion of the airway (the "upper airway") consists of two passageways, the nasal airway and the oral airway. These two passageways merge to become a single passageway. Portions of the upper airway just behind the tongue are known as the soft palate, the pharynx, the hypopharynx, etc.

In persons affected by OSA, closure, reduction in patency or increased airflow resistance of the upper airway occurs during sleep, due to a combination of physiological changes associated with sleep (including relaxation of muscles) and the anatomy of the upper airway (which is generally smaller or more crowded than in normal individuals). In persons prone to sleep apnea, a portion or portions of the muscular walls of the upper airway may become narrow or collapse, leading to reduction in airflow ("hypopnea"), cessation of airflow ("apnea"), increase in airflow turbulence or increased resistance to airflow within the airway. In the instance of collapse, the upper airway is blocked, breathing stops, air movement to the lungs ceases, and the oxygen level in the blood tends to decrease. As a response to this process (or to less severe manifestations, such as hypopneas or increased airway resistance), a brief arousal usually occurs in the brain. As a consequence of the brief arousal, the muscle tone in the walls of the upper airway returns to waking levels, and the airway abnormality is corrected—i.e. airway resistance and patency return to normal levels.

Generally, following each event, the patient returns to sleep, until another partial or complete upper airway collapse occurs and the process repeats itself. Depending on the severity in an individual case, the number of events may range from a few per hour of sleep to more than 100 events per hour of sleep. This process disrupts normal sleep. As a consequence, patients typically suffer from the effects of sleep deprivation. Such effects may include daytime drowsiness, tiredness or fatigue, difficulties with mental concentration or memory, mood changes, reductions in performance or increases in mistakes, and increased risk of accidents. Additionally, OSA is known to increase the risk of development of other medical problems.

Snoring is a mild form of sleep-disordered breathing in which increased airflow turbulence occurs. The snoring sounds result from tissue vibration within the nasal or oral airway. While snoring has been traditionally regarded as a social or cosmetic problem, recent studies suggest that snoring may be linked to the development of health problems, including high blood pressure.

Airway closure during sleep generally occurs at one or both of two levels in the upper airway: the soft palate and the hypopharynx (base of the tongue). At either level, the anterior tissue can collapse against the posterior pharyngeal wall, which makes up the rear wall of the throat. Additionally, the side (lateral) walls of the upper airway can collapse inward partially, or completely against each other. The lateral walls of the airway are susceptible to collapse in many patients with obstructive sleep apnea and other forms of sleep-related breathing disorders. In these cases, prevention of collapse of the airway only in the anterior-posterior dimension is insufficient to maintain normal airway patency. Even after extensive airway surgery for sleep apnea (which primarily addresses the anterior-posterior dimension of the airway), the patient may continue to have problems with breathing during sleep, due to lateral wall collapse or dysfunction.

Several types of treatment are available for obstructive sleep apnea and other sleep-related breathing disorders. The most common treatment consists of an air pressure delivery system that applies greater than atmospheric pressure to all walls of the upper airway to reduce the potential for full or partial collapse. Many people have difficulty using this device or prefer not to use it for various reasons. Also, surgical reconstruction of the airway or dental devices may be used. These treatments, however, often fail to treat the problem adequately.

Accordingly, a need exists in the art for an improved method and system for treating sleep apnea and other sleep-related breathing disorders.

SUMMARY OF THE INVENTION

Embodiments of the present invention are generally directed to a system for treating sleep-related breathing disorders. In one embodiment, the system includes a first magnet attached to a left lateral pharyngeal wall, and a second magnet attached to a right lateral pharyngeal wall. The second magnet is positioned opposite the first magnet across an upper airway.

In another embodiment, the system includes a first magnetically susceptible material attached to a left lateral pharyngeal wall and a second magnetically susceptible material attached to a right lateral pharyngeal wall. The second magnetically susceptible material is positioned opposite the first magnetically susceptible material across an upper airway. The system further includes a first magnet disposed outside the body and lateral to the first magnetically susceptible material, and a second magnet disposed outside the body and lateral to the second magnetically susceptible material.

In yet another embodiment, the system includes a first magnet attached to a left lateral pharyngeal wall and a second magnet attached to a right lateral pharyngeal wall. The second magnet is positioned opposite the first magnet across an upper airway. The system further includes a third magnet disposed inside the upper airway directly across from the first magnet and a fourth magnet disposed inside the upper airway directly across from the second magnet.

BRIEF DESCRIPTION OF THE DRAWINGS

The following detailed description makes reference to the accompanying drawings, which are now briefly described.

While the invention is described herein by way of example for several embodiments and illustrative drawings, those skilled in the art will recognize that the invention is not limited to the embodiments or drawings described. It should be understood, that the drawings and detailed description thereto are not intended to limit the invention to the particular form disclosed, but on the contrary, the intention is to cover all modifications, equivalents and alternatives falling within the spirit and scope of the present invention as defined by the appended claims. The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including, but not limited to.

DETAILED DESCRIPTION

Figure 1A:
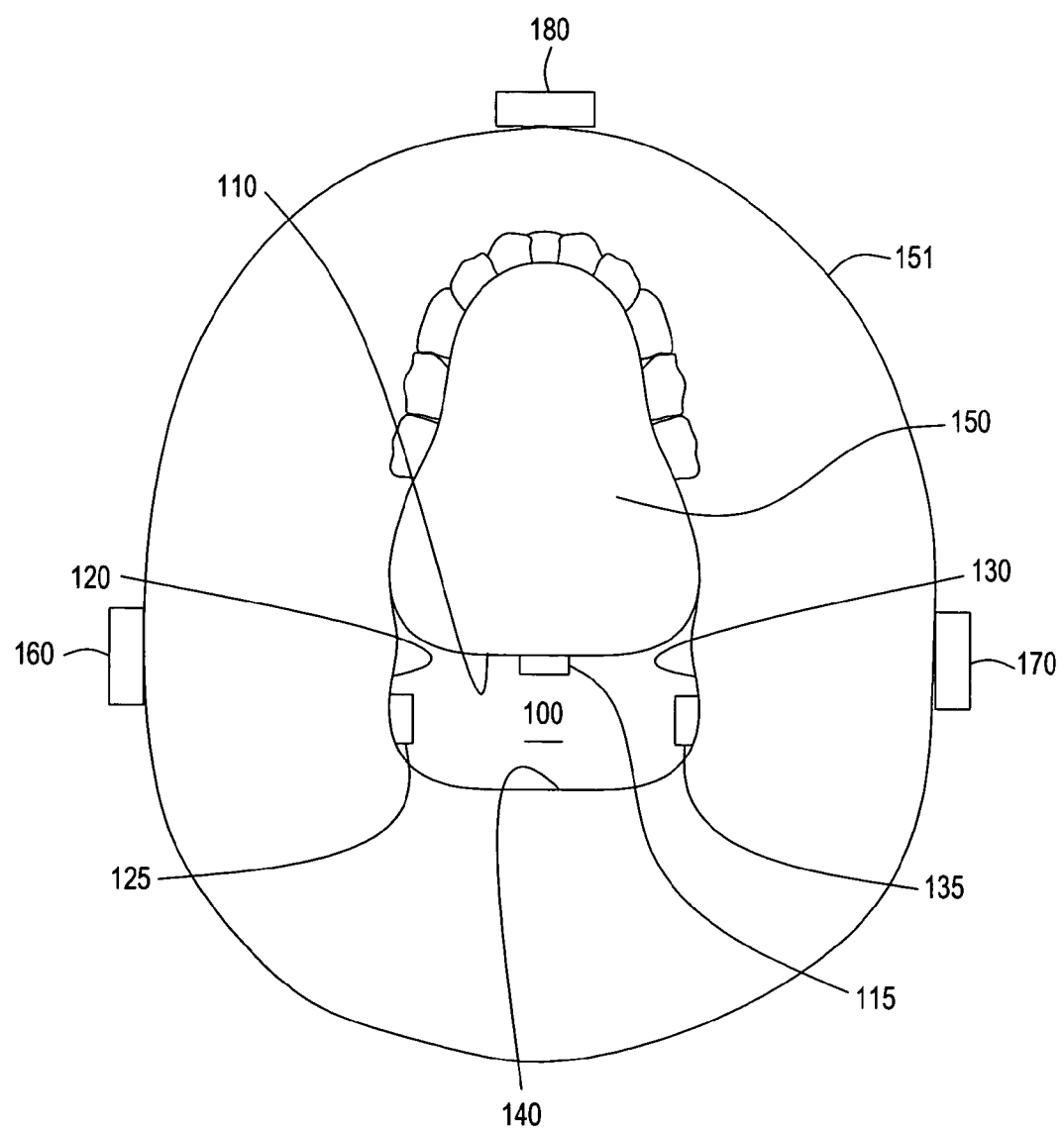
FIG. 1A, 1B, 3, 4, 5A and 5B illustrate a series of coronal views of an upper airway, each having a system for treating sleep-related breathing disorders in accordance with one embodiment of the invention.
Figure 1B:
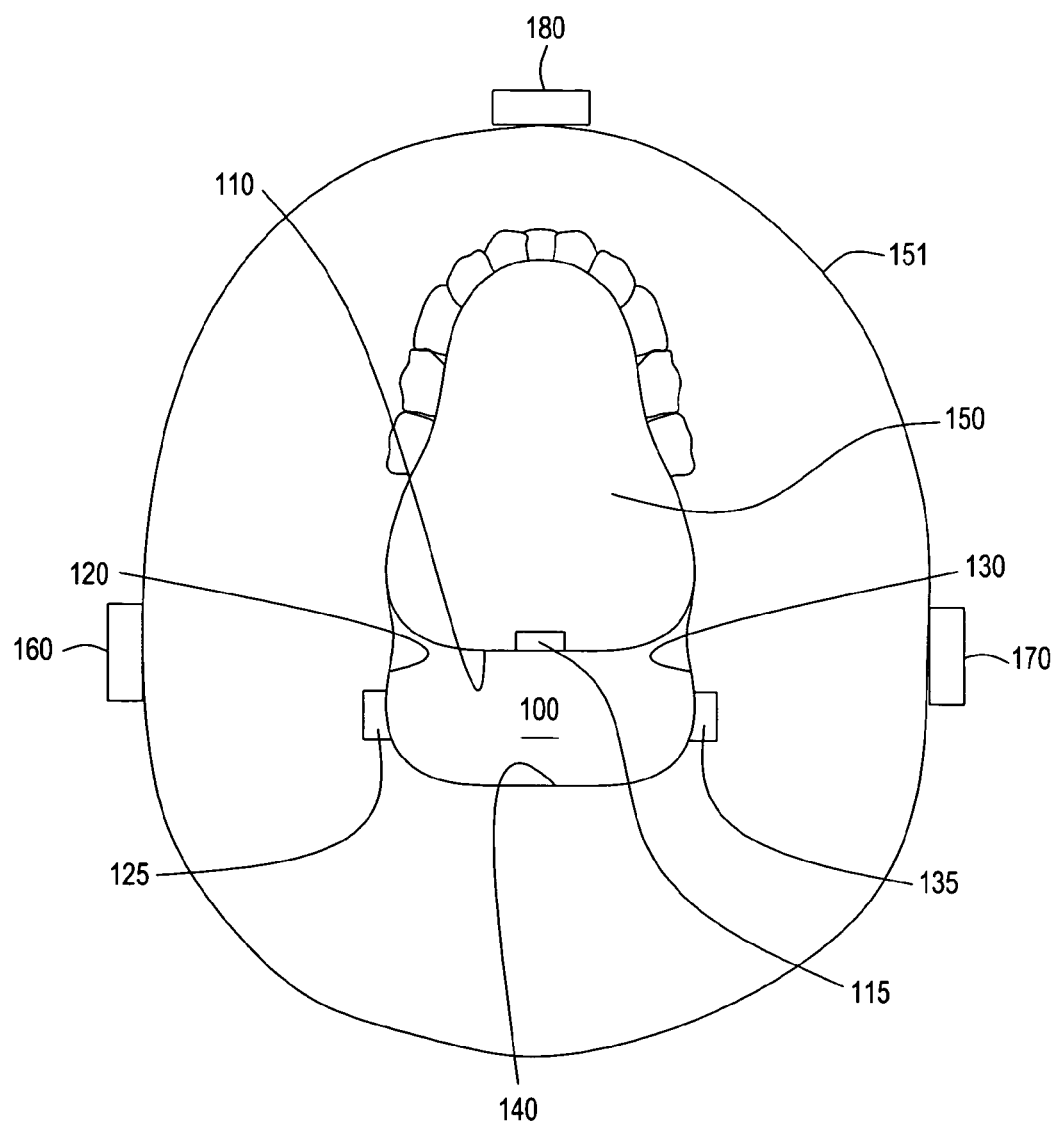

FIG. 1A illustrates a coronal view of an upper airway 100 having a system for treating sleep apnea (and other sleep-related breathing disorders, e.g., snoring) in accordance with one embodiment of the invention. The upper airway 100 is generally defined by the anterior pharyngeal wall 110, two lateral pharyngeal walls 120, 130 and the posterior pharyngeal wall 140. The lateral pharyngeal walls 120, 130 generally include lateral pharyngeal tissue extending superiorly to the velopharynx and inferiorly to the epiglottis. The posterior pharyngeal wall 140 generally includes posterior pharyngeal tissue extending superiorly to the velopharynx and inferiorly to the epiglottis. The anterior pharyngeal wall 110 generally includes a base portion of the tongue 150, the soft palate 210 and the uvula 220 (shown in FIG. 2). Magnetically susceptible material 115 is attached to the anterior pharyngeal wall 110, magnetically susceptible material 125 is attached to the lateral pharyngeal wall 120, and magnetically susceptible material 135 is attached to the lateral pharyngeal wall 130. In one embodiment, magnetically susceptible materials 115, 125, 135 are attached to the respective pharyngeal walls by surgical sutures or bonding material, such as surgical glue. Other means for attaching the magnetically susceptible materials to the pharyngeal walls are also contemplated by embodiments of the invention described herein. In another embodiment, the magnetically susceptible materials 115, 125, 135 may be implanted inside, or embedded beneath the surface of, the respective pharyngeal walls, as shown in FIG. 1B. In yet another embodiment, the magnetically susceptible materials 115, 125, 135 may be coated on the surfaces of the respective pharyngeal walls.

The magnetically susceptible materials 115, 125, 135 may be materials, which are not magnets, but are susceptible to magnetic fields, such as ferromagnetic materials. As such, magnetically susceptible materials 115, 125, 135 would not interact with each other in the absence of a magnetic field, such as, during daytime, as opposed to permanent magnets that would potentially interact with each other at all times, which may be inappropriate or even deleterious (e.g., during speaking or swallowing) to a person's health. Magnetically susceptible materials 115, 125, 135 may be in the form of plates, discs, spheres, bars, multiple small pieces, mesh and the like. In an alternate embodiment, the magnetically susceptible materials 115, 125, 135 may be replaced with magnets, such as permanent magnets with magnetic fields of fixed strength or variable magnets (e.g., electromagnets) with magnetic fields of variable strength (including zero if not activated).

Figure 2:
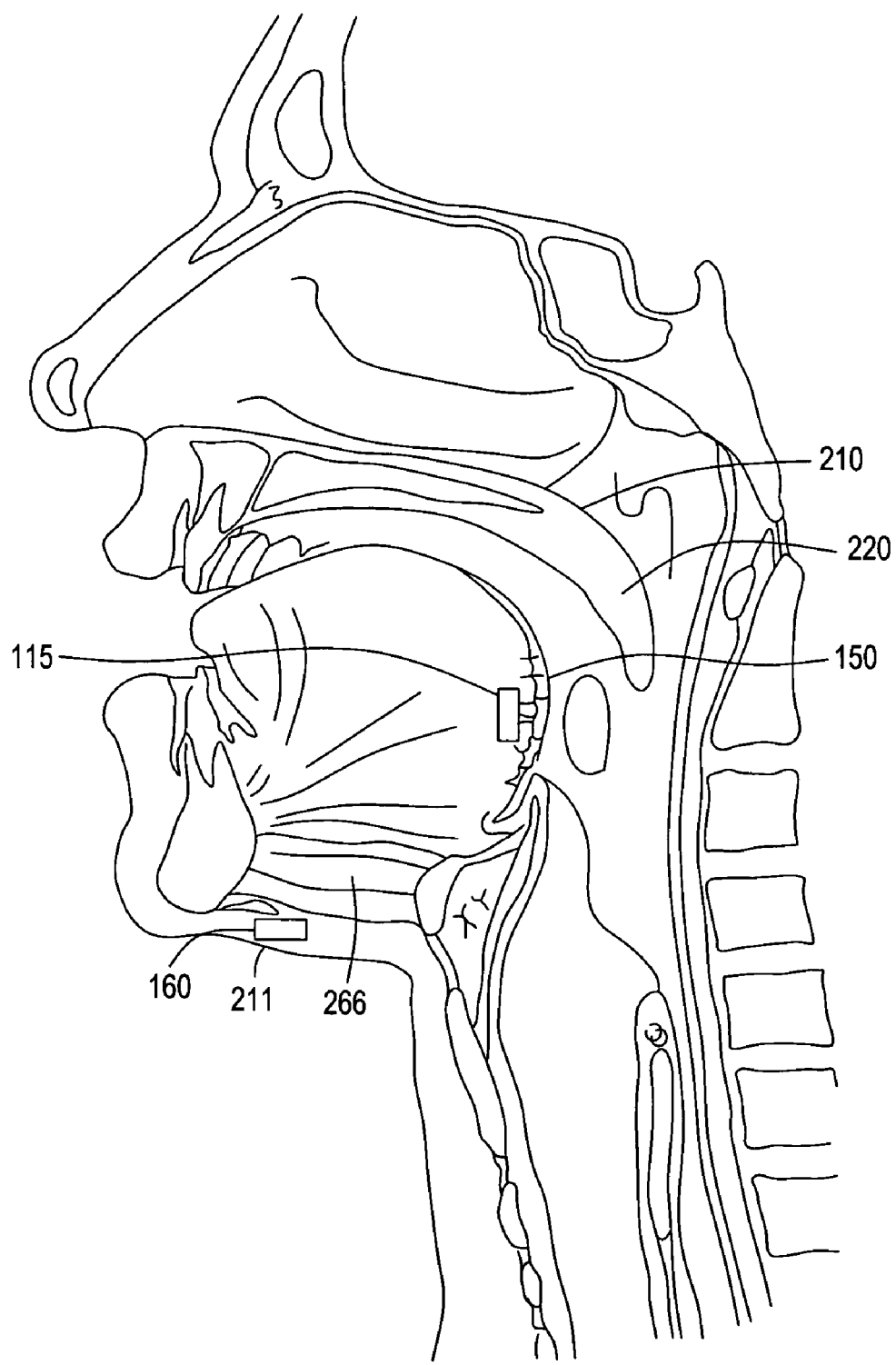
FIG. 2 illustrates a sagittal view of the upper airway having a system for treating sleep-related breathing disorders in accordance with one embodiment of the invention.

Magnet 160 is positioned outside the body and lateral to magnetically susceptible material 125, while magnet 170 is positioned outside the body and lateral to magnetically susceptible material 135, and magnet 180 is positioned outside the body and anterior to magnetically susceptible material 115. Magnets 160, 170, 180 may be attached or placed adjacent to the outer skin 151 of a patient with means, such as a neckband or a chin strap. In one embodiment, magnets 160, 170, 180 may be implanted beneath the outer skin surface, such as, beneath the front skin 211 of the cheek 266 for magnet 160, as shown in FIG. 2.

Magnet 160 is configured to attract magnetically susceptible material 125 toward magnet 160 so that movement of the lateral pharyngeal wall 120 toward closure of the upper airway 100 may be opposed. Magnet 170 is configured to attract magnetically susceptible material 135 toward magnet 170 so that movement of the lateral pharyngeal wall 130 toward closure of the upper airway 100 may be opposed. Magnet 180 is configured to attract magnetically susceptible material 115 toward magnet 180 so that movement of the anterior pharyngeal wall 110 toward closure of the upper airway 100 may be opposed. In this manner, the cross sectional dimensions (e.g., the length or width) of the upper airway 100 may be increased or prevented from decreasing, thereby allowing patency of the upper airway 100 to be maintained.

Force fields between magnet 160 and magnetically susceptible material 125 and between magnet 170 and magnetically susceptible material 135 act to keep the soft tissue of the lateral pharyngeal walls 120, 130 from collapsing. Force fields between magnet 180 and magnetically susceptible material 115 act to keep the soft tissue of the anterior pharyngeal wall 110 from collapsing toward the posterior pharyngeal wall 140.

Figure 3:
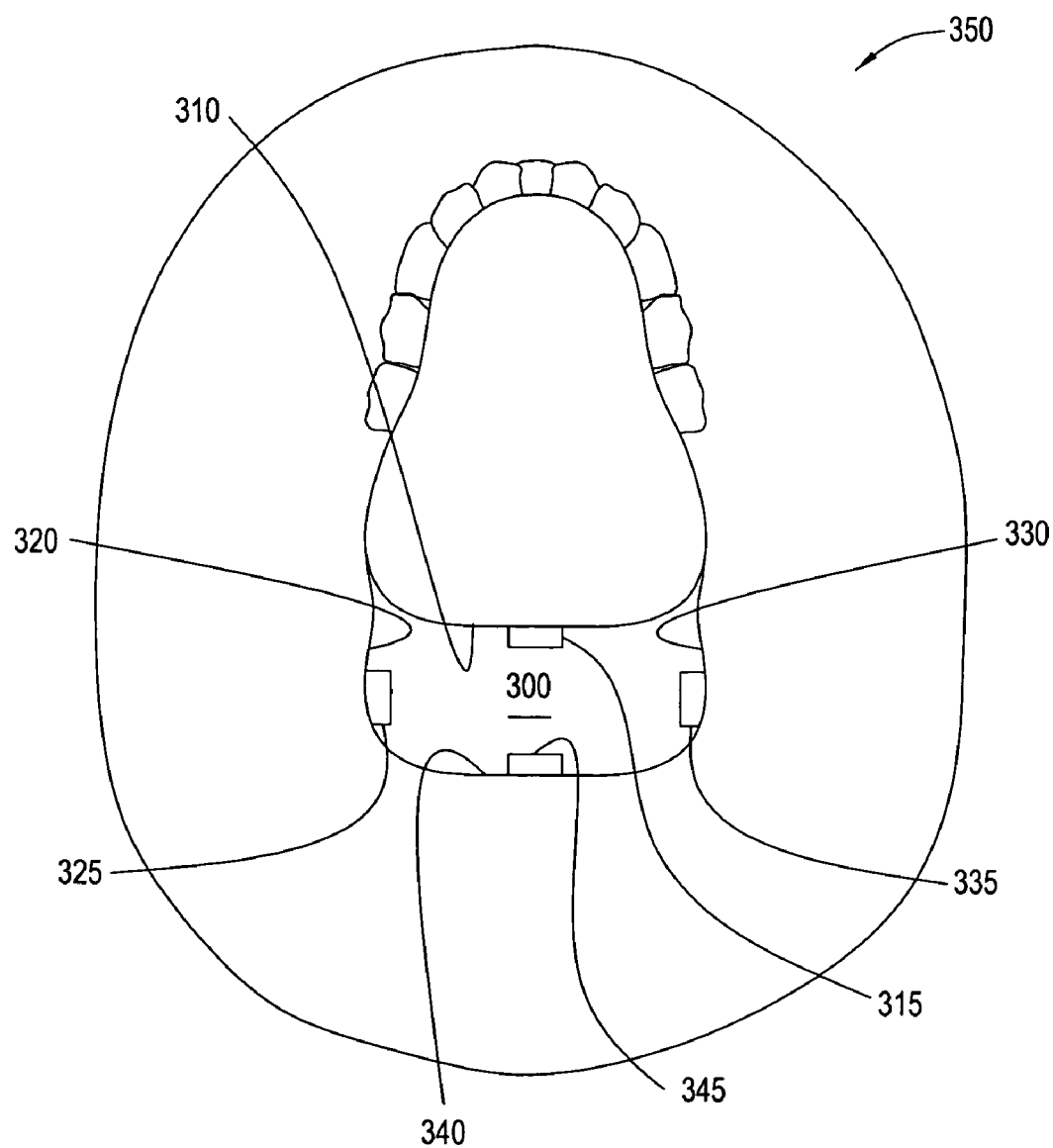

FIG. 3 illustrates a coronal view of an upper airway 300 having a system 350 for treating sleep apnea (and other sleep-related breathing disorders, e.g., snoring) in accordance with another embodiment of the invention. The system 350 includes magnet 315 attached to an anterior pharyngeal wall 310, magnet 325 attached to lateral pharyngeal wall 320, magnet 335 attached to lateral pharyngeal wall 330, and magnet 345 attached to posterior pharyngeal wall 340. In one embodiment, magnets 315, 325, 335, 345 are attached to the respective pharyngeal walls by surgical sutures or bonding material, such as surgical glue. Other means for attaching the magnets to the pharyngeal walls are also contemplated by embodiments of the invention described herein. In another embodiment, magnets 315, 325, 335, 345 may be implanted inside (e.g., embedded beneath the surface of) the respective pharyngeal walls. In yet another embodiment, magnets 315, 325, 335, 345 may be coated on surfaces of the respective pharyngeal walls.

Magnets 315, 325, 335, 345 may be permanent magnets with magnetic fields of fixed strength or variable magnets, such as electro-magnets, with magnetic fields of variable strength (including zero if not activated).

Magnets 315, 325, 335, 345 are oriented such that the same magnetic poles of the magnets 315, 325, 335, 345 face each other, e.g., north poles facing other north poles. In operation, magnets 315, 325, 335, 345 are configured to repel each other, thereby opposing closure of the upper airway 300 without the use of external magnets.

Figure 4:
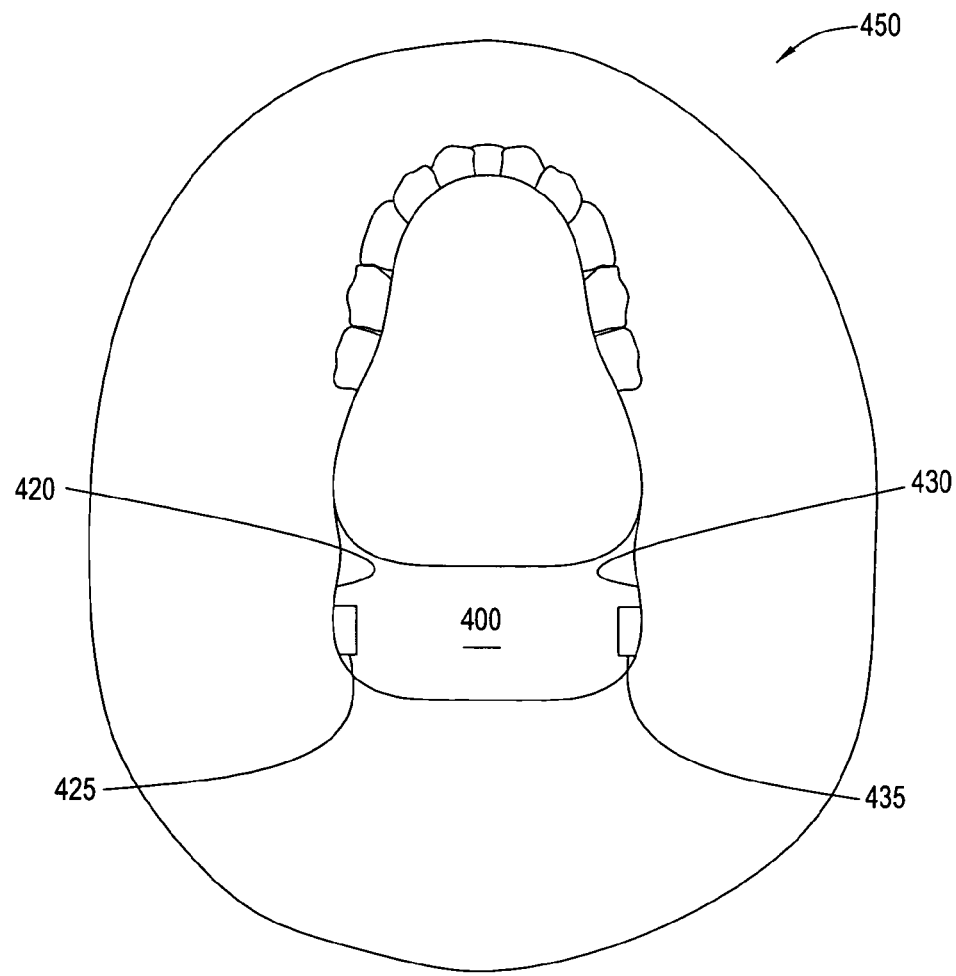

FIG. 4 illustrates a coronal view of an upper airway 400 having a system 450 for treating sleep apnea (and other sleep-related breathing disorders, e.g., snoring) in accordance with yet another embodiment of the invention. The system 450 includes magnet 425 attached to lateral pharyngeal wall 420 and magnet 435 attached to lateral pharyngeal wall 430. In one embodiment, magnets 425, 435 are attached to the respective lateral pharyngeal walls by surgical sutures or bonding material, such as surgical glue. Other means for attaching the magnets to the lateral pharyngeal walls are also contemplated by embodiments of the invention described herein. In another embodiment, magnets 425, 435 may be implanted inside (e.g., embedded beneath the surface of) the respective lateral pharyngeal walls. In yet another embodiment, magnets 425, 435 may be coated on surfaces of the respective lateral pharyngeal walls.

Magnets 425, 435 may be permanent magnets with magnetic fields of fixed strength or variable magnets, such as electromagnets, with magnetic fields of variable strength (including zero if not activated). Magnets 425, 435 are oriented such that the same magnetic poles of the magnets 425, 435 face each other, e.g., north pole facing other north pole. In operation, magnets 425, 435 are configured to repel each other, thereby opposing closure of the upper airway 400 without the use of external magnets.

Figure 5:
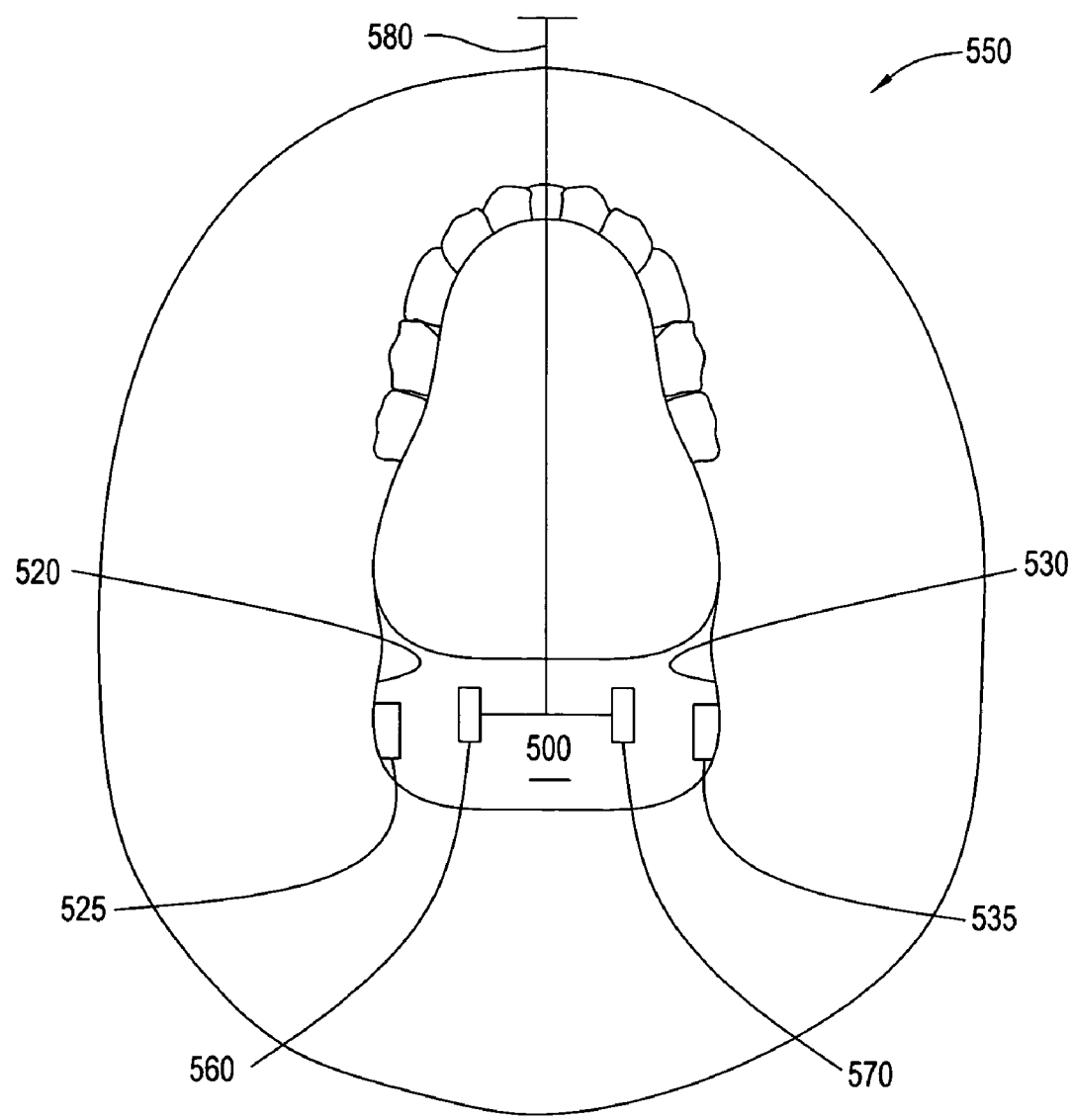
Figure 5A:
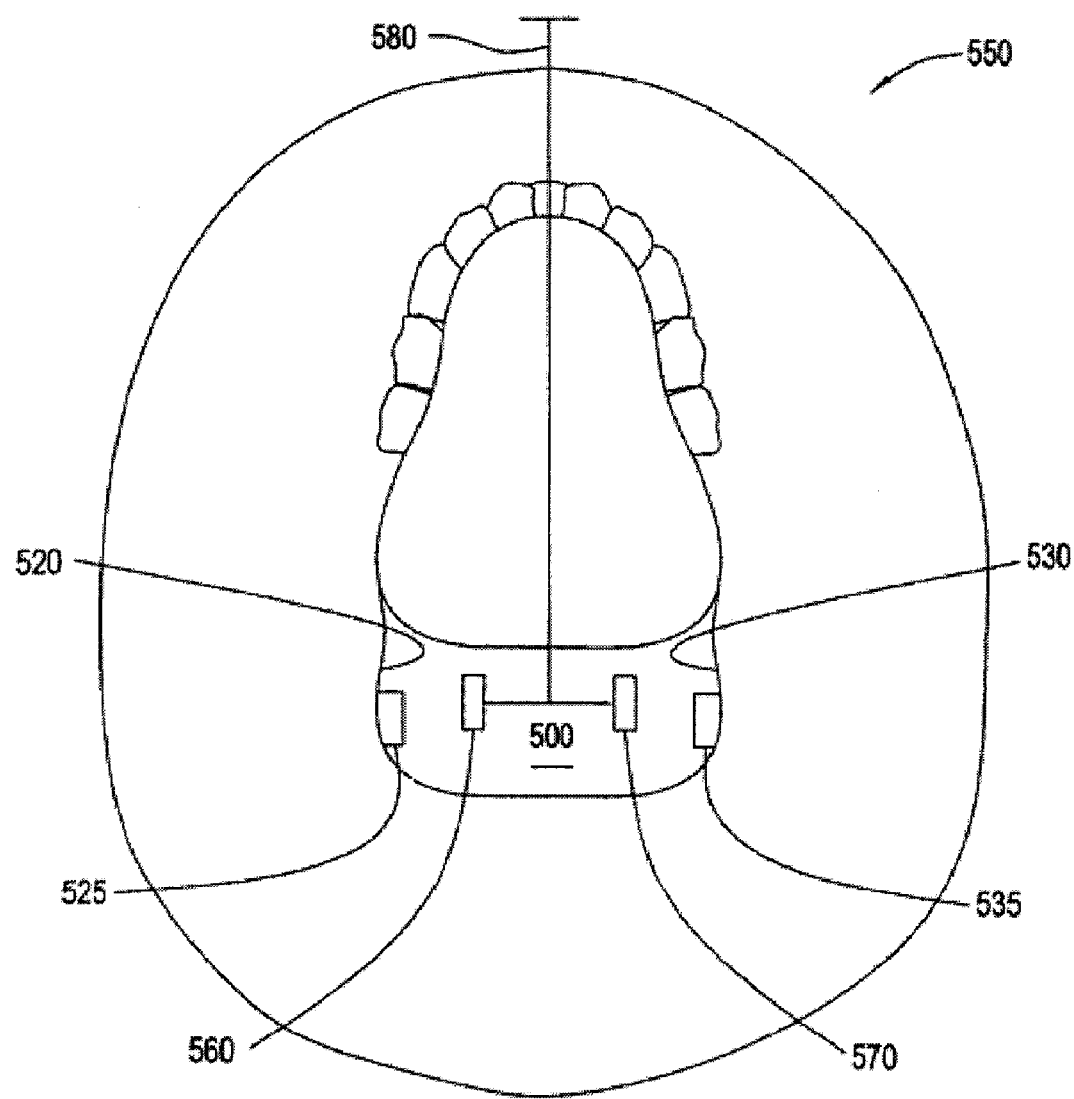
Figure 5B:
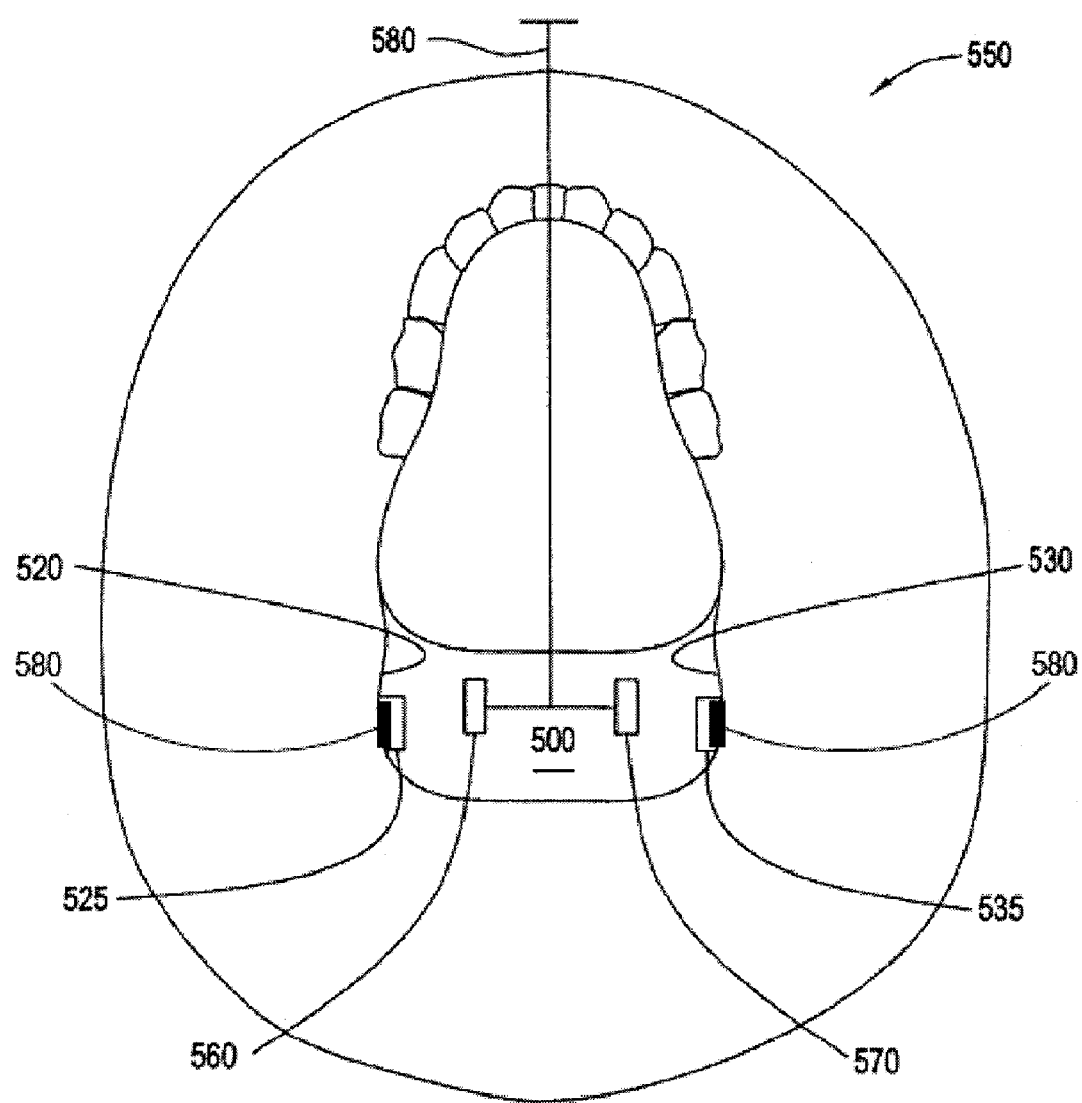

FIGS. 5A and 5B illustrates a system 550 for treating sleep apnea (and other sleep-related breathing disorders, e.g. snoring) disposed inside an upper airway 500 in accordance with still another embodiment of the invention. The system 550 includes magnet 525 attached to lateral pharyngeal wall 530. In one embodiment shown in FIG. 5B, magnets 525, 535 may be attached to the lateral pharyngeal walls 520, 530, by surgical sutures or bonding material 580, such as surgical glue. Other means for attaching the magnets to the pharyngeal walls are also contemplated by embodiments of the invention described herein. In another embodiment, magnets 525, 535 may be implanted inside the lateral pharyngeal walls 520, 530. In yet another embodiment, magnets 525, 535 may be coated on surfaces of the lateral pharyngeal walls 520, 530. Magnets 525, 535 may be permanent magnets with magnetic fields of fixed strength or variable magnets, such as electro-magnets, with magnetic fields of variable strength (including zero if not activated).

The system 550 further includes magnets 560 and 570 disposed inside the upper airway 500. Magnet 560 is disposed across from magnet 525, while magnet 570 is disposed across from magnet 535. The magnetic poles of magnets 560, 570 are oriented such that magnets 560, 570 repel magnets 525, 535, respectively, thereby opposing closure of the upper airway 500 without the use of external magnets. Magnets 560, 570 may be attached to or held in place by a removable apparatus 580, such as a mouthpiece.

Each magnet or magnetically susceptible material described herein may comprise more than one magnet or magnetically susceptible material. Although embodiments of the invention have been described with reference to two or four magnetically susceptible materials or magnets, embodiments of the invention also contemplate other combinations or numbers of magnets and magnetically susceptible materials. Although embodiments of the invention have been described with reference to treating sleep-related breathing disorders, such as sleep apnea or snoring, embodiments of the invention also contemplate other applications where passageway or airway patency is required. For example, the magnets or magnetically susceptible materials may be inserted or attached through a body aperture, such as the vagina, the rectum, the urinary passage and the like.

While the foregoing is directed to embodiments of the present invention, other and further embodiments of the invention may be devised without departing from the basic scope thereof, and the scope thereof is determined by the claims that follow.

What is claimed is:

1. A system for preventing sleep apnea and other sleep-related breathing disorders, comprising: a first magnet attached to a left lateral pharyngeal wall; a second magnet attached to a right lateral pharyngeal wall, wherein the second magnet is positioned opposite the first magnet across an upper airway; a third magnet disposed inside the upper airway directly across from the first magnet; and a fourth magnet disposed inside the upper airway directly across from the second magnet.

2. The system of claim 1, wherein the third magnet generates a magnetic field that repels the first magnet away from the third magnet, and wherein the fourth magnet generates a magnetic field that repels the second magnet away from the fourth magnet.

3. The system of claim 1, wherein the third and fourth magnets are attached to a removable apparatus to hold the third and fourth magnets inside the upper airway.

4. The system of claim 1, wherein the first and the second magnet are attached to the left and right lateral pharyngeal walls by surgical sutures or bonding material.

5. The system of claim 1, wherein the first and second magnets are one of permanent and variable magnets.

6. A method for treating sleep-related breathing disorders, comprising: attaching a first magnet to a left lateral pharyngeal wall; attaching a second magnet to a right lateral pharyngeal wall opposite the first magnet across an upper airway; disposing a third magnet inside the upper airway directly across from the first magnet; and disposing a fourth magnet inside the upper airway directly across from the second magnet.

7. The method of claim 6, further comprising: repelling the first magnet away from the third magnet; and repelling the second magnet away from the fourth magnet.

* * * * *